United States Patent
Pulkkinen et al.

(10) Patent No.: US 11,771,367 B1
(45) Date of Patent: Oct. 3, 2023

(54) SLEEP SCORES

(71) Applicant: Amazon Technologies, Inc., Seattle, WA (US)

(72) Inventors: Pekka Pietari Pulkkinen, Sammamish, WA (US); Haithem Albadawi, Redmond, WA (US); Yan Zhang, Bellevue, WA (US)

(73) Assignee: Amazon Technologies, Inc., Seattle, WA (US)

( * ) Notice: Subject to any disclaimer, the term of this patent is extended or adjusted under 35 U.S.C. 154(b) by 444 days.

(21) Appl. No.: 16/677,526

(22) Filed: Nov. 7, 2019

(51) Int. Cl.
 *A61B 5/00* (2006.01)
 *G16H 50/00* (2018.01)
 *G16H 50/30* (2018.01)

(52) U.S. Cl.
 CPC ............ *A61B 5/4815* (2013.01); *A61B 5/4809* (2013.01); *A61B 5/4812* (2013.01); *A61B 5/7264* (2013.01); *A61B 5/742* (2013.01); *G16H 50/00* (2018.01); *G16H 50/30* (2018.01)

(58) Field of Classification Search
 CPC ... A61B 5/4815; A61B 5/4809; A61B 5/4812; A61B 5/7264; A61B 5/742; G16H 50/00; G16H 50/30
 See application file for complete search history.

(56) References Cited

U.S. PATENT DOCUMENTS

| 10,098,582 | B1 * | 10/2018 | McNair et al. ....... | A61B 5/4812 |
| 2010/0099954 | A1 * | 4/2010 | Dickinson et al. ..... | G09B 19/00 600/300 |

(Continued)

FOREIGN PATENT DOCUMENTS

| WO | 2008096307 A1 * | 8/2008 | ............... A61B 5/0002 |
| WO | 2013186265 A1 * | 12/2013 | ............... A61B 5/4812 |

(Continued)

OTHER PUBLICATIONS

Anguelov, D., Srinivasan, P., Koller, D., Thrun, S., Rodgers, J. and Davis, J., "SCAPE: Shape Completion and Animation of People," ACM Trans. Graph. (Proc. SIGGRAPH), 24(3):408-416, Jul. 2005, 9 pages, http://robots.stanford.edu/papers/anguelov.shapecomp.pdf Balan, A. O. and Black, M. J., "The Naked Truth: Estimating Body Shape under Clothing," In European Conference on Computer Vision (ECCV), 2008, 15 pages, https://www.researchgate.net/profile/Michael_Black6/publication/221305001_The_Naked_Truth_Estimating_Body_Shape_Under_Clothing/links/0fcfd512d21f538458000000/The-Naked-Truth-Estimating-Body-Shape-Under-Clothing.pdf?origin=publication detail.

(Continued)

*Primary Examiner* — Evangeline Barr
(74) *Attorney, Agent, or Firm* — Athorus, PLLC

(57) ABSTRACT

Described are systems and methods for generating sleep scores based at least in part on the visual appearance of hypnograms. The disclosed implementations generate an embedding vector representative of the visual appearance of a hypnogram and utilize that embedding to determine a sleep score of the sleep session represented by the hypnogram. For example, a deep neural network, such as a convolutional neural network ("CNN"), may be trained with input data that includes hypnograms that have been labeled according to their sleep quality, or sleep score. The trained network may then be provided with an unlabeled hypnogram, generate an embedding representative of that hypnogram, and determine a sleep score corresponding to that hypnogram.

19 Claims, 13 Drawing Sheets

(56) References Cited

U.S. PATENT DOCUMENTS

| | | | |
|---|---|---|---|
| 2013/0251269 A1* | 9/2013 | Chehaiber | G06V 10/462 382/197 |
| 2017/0055899 A1* | 3/2017 | Bandyopadhyay et al. | A61B 5/4815 |
| 2019/0099582 A1* | 4/2019 | Crow et al. | A61B 5/1116 |

FOREIGN PATENT DOCUMENTS

| | | | |
|---|---|---|---|
| WO | 2018011801 A1* | 1/2018 | A61B 5/7264 |
| WO | 2018070935 A1* | 4/2018 | G16H 50/70 |

OTHER PUBLICATIONS

Balan, A. O., Sigal, L., Black, M. J., Davis, J. E. and Haussecker, H. W., "Detailed Human Shape and Pose from Images," In IEEE Conference on Computer Vision and Pattern Recognition (CVPR), 2007, 9 pages.

Bogo, F., Kanazawa, A., Lassner, C., Gehler, P., Romero, J. and Black, M. J., "Keep it SMPL: Automatic Estimation of 3D Human Pose and Shape from a Single Image," In European Conference on Computer Vision (ECCV) 2016, 21 pages, https://arxiv.org/pdf/1607.08128v1.pdf.

Chen, X., Guo, Y., Zhou, B. and Zhao, Q., "Deformable Model for Estimating Clothing and Naked Human Shapes from a Single Image," The Visual Computer, 29(11):1187-1196, 2013, 10 pages.

Chen, Y., Kim, T.-K. and Cipolla, R., "Inferring 3D Shapes and Deformations from Single Views," In European Conference on Computer Vision, 2010, 14 pages.

Chen, Y., Kim, T.-K. and Cipolla, R., "Silhouette-Based Object Phenotype Recognition Using 3D Shape Priors. In Inter-national Conference on Computer Vision (ICCV), 2011, 8 pages.

Devries, T. and Taylor, G. W., "Learning Confidence for Out-of-Distribution Detection in Neural Networks, arXiv preprint arXiv:1802.04865, 2018, 12 pages.

Dibra, E., Jain, H., Öztireli, C., Ziegler, R. and Gross, M., "HSNets: Estimating Human Body Shape from Silhouettes with Convolutional Neural Networks," In International Conference on 3D Vision (3DV), 2016, 10 pages.

Dibra, E., Jain, H., Öztireli, C., Ziegler, R. and Gross, M., "Human Shape from Silhouettes Using Generative HKS Descriptors and Cross-Modal Neural Networks," In IEEE Conference on Computer Vision and Pattern Recognition (CVPR), 2017, 11 pages.

Dibra, E., Jain, H., Öztireli, C., Ziegler, R. and Gross, M., "Shape from Selfies: Human Body Shape Estimation Using CCA Regression Forests," In European Converence on Computer Vision (ECCV), 2016, 17 pages.

Gilbert, A., Volino, M., Collomosse, J. and Hilton, A., "Volumetric Performance Capture from Minimal Camera View-Points," In European Conference on Computer Vision, 2018, 16 pages.

Gong, K., Liang, X., Zhang, D., Shen, X. and Lin, L., "Look into Person: Self-Supervised Structure-Sensitive Learning and a New Benchmark for Human Parsing," In IEEE Conference on Computer Vision and Pattern Recognition (CVPR), 2017, 9 pages.

Guan, P., Weiss, A., Balan, A. O. and Black, M. J., "Estimating Human Shape and Pose from a Single Image," In IEEE International Conference on Computer Vision (ICCV), 2009, 8 pages.

Güler, R. A., Neverova, N. and Kokkinos, I., "DensePose: Dense Human Pose Estimation in the Wild," In IEEE Conference on Computer Vision and Pattern Recognition (CVPR), 2018, 10 pages.

He, K., Zhang, X., Ren, S. and Sun, J., "Deep Residual Learning for Image Recognition," In IEEE Conference on Computer Vision and Pattern Recognition (CVPR), 2016, 9 pages.

Horprasert, T., Harwood, D. and Davis, L. S., "A Statistical Approach for Real-Time Robust Background Subtraction and Shadow Detection," In IEEE International Conference on Computer Vision (ICCV), 1999, 19 pages.

Joo, H., Simon, T. and Y. Sheikh, Y., "Total Capture: A 3D Deformation Model for Tracking Faces, Hands, and Bodies," In IEEE Conference on Computer Vision and Pattern Recognition (CVPR), 2018, 10 pages.

Kanazawa, A., Black, M. J., Jacobs, D. W. and Malik, J., "End-to-End Recovery of Human Shape and Pose," In IEEE Conference on Computer Vision and Pattern Recognition (CVPR), 2018, 10 pages.

Kundu, A., Li, Y. and Rehg, J. M., "3D-RCNN: Instance-Level 3D Object Reconstruction via Render-and-Compare," In IEEE Conference on Computer Vision and Pattern Recognition (CVPR), 2018, 10 pages.

Lassner, C., Romero, J., Kiefel, M., Bogo, F., Black, M. J. and Gehler, P. V., "Unite the People - Closing the Loop Between 3D and 2D Human Representations," In IEEE Conference on Computer Vision and Pattern Recognition (CVPR), 2017, 10 pages.

Long, J., Shelhamer, E., and Darrell, T., "Fully Convolutional Networks for Semantic Segmentation, "In IEEE Conference on Computer Vision and Pattern Recognition (CVPR), 2015, 10 pages.

Loper, M., Mahmood, N., Romero, J., Pons-Moll, G. and Black, M. J., "SMPL: A Skinned Multi-Person Linear Model," ACM Trans. Graphics (Proc. Siggraph Asia), 34(6):248-1-248:16, Oct. 2015, 16 pages.

Ngiam, J., Khosla, A., Kim, M., Nam, J., Lee, H.and Ng, A. Y., "Multimodal Deep Learning," In International Conference on Machine Learning (ICML), pages 689-696, 2011, 8 pages.

Omran, M., Lassner, C., Pons-Moll, G., Gehler, P. V. and Schiele, B., "Neural Body Fitting: Unifying Deep Learning and Model-Based Human Pose and Shape Estimation," In International Conference on 3D Vision (3DV), 2018, 13 pages.

Pavlakos, G., Zhu, L., Zhou, X. and Daniilidis, K., "Learning to Estimate 3D Human Pose and Shape from a Single Color Image," In IEEE Conference on Computer Vision and Pattern Recognition (CVPR), 2018, 10 pages.

Popa, A.-I., Zanfir, M. and C. Sminchisescu, C., "Deep Multitask Architecture for Integrated 2D and 3D Human Sensing," In IEEE Conference on Computer Vision and Pattern Recognition (CVPR), 2017, 10 pages.

Rhodin, H., Robertini, N., Casas, D., Richardt, C., Seidel, H.-P. and Theobalt, C., "General Automatic Human Shape and Motion Capture Using Volumetric Contour Cues," In European Conference on Computer Vision, 2016, 18 pages.

Robinette, K. M., Blackwell, S., Daanen, H., Boehmer, M., Fleming, S., Brill, T., Hoeferlin, D. and Burnsides, D., "Civilian American and European Surface Anthropometry Resource (CAESAR) Final Report," Tech. Rep. AFRL-HEWP-TR-2002-0169, US Air Force Research Laboratory, 2002, 70 pages.

Sigal, L., Balan, A. O. and Black, M. J., "Combined Discriminative and Generative Articulated Pose and Non-Rigic Shape Estimation," In Neural Information Processing Systems (NIPS), 2007, 8 pages.

Sun, J., Ovsjanikov, M. and Guibas, L., "A Concise and Provably Informative Multi-Scale Signature Based on Heat Diffusion," In Symposium on Geometry Processing, 2009, 10 pages.

Tan, J. K. V., Budvytis, I. and Cipolla, R., "Indirect Deep Structured Learning for 3D Human Body Shape and Pose Prediction," In British Machine Vision Conference, 2017, 11 pages.

Varol, G., Ceylan, D., Russell, B., Yang, J., Yumer, E., Laptev, I. and Schmid, C., "BodyNet: Volumetric Inference of 3D Human Body Shapes," In European Conference on Computer Vision (ECCV), 2018, 17 pages.

Varol, G., Romero, J., Martin, X., Mahmood, N., Black, M. J., Laptev, I. and Schmid, C., "Learning from Synthetic Humans," In IEEE Conference on Computer Vision and Pattern Recognition (CVPR), 2017, 9 pages.

Xi, P., Lee, W.-S. and Shu, C., "A Data-Driven Approach to Human-Body Cloning Using a Segmented Body Database," In Pacific Conference on Computer Graphics and Applications (PG), 2007, 9 pages.

Yu, F., Zhang, Y., Song, S., Seff, A., and Xiao, J., "LSUN: Construction of a Large-Scale Image Dataset Using Deep Learning with Humans in the Loop," arXiv preprint arXiv:1506.03365, 2015, 9 pages.

(56) References Cited

OTHER PUBLICATIONS

Zanfir, A., Marinoiu, E. and Sminchisescu, C., "Monocular 3D Pose and Shape Estimation of Multiple People in Natural Scenes - the Importance of Multiple Scene Constraints," In IEEE Conference on Computer Vision and Pattern Recognition (CVPR), 2018, 10 pages.

Zhang, H., Dana, K., Shi, J., Zhang, Z., Wang, X., Tyagi, A. and Agrawal, A., "Context Encoding for Semantic Segmentation," In The IEEE Conference on Computer Vision and Pattern Recognition (CVPR), Jun. 2018, 10 pages.

Boisvert, J., Shu, C., Wuhrer, S., and Xi, P., "Three-Dimensional Human Shape Inference from Silhouettes: Reconstruction and Validation," Machine Vision and Applications, 24(1):145-157, 2013, 13 pages, http://people.scs.carleton.ca/~c_shu/Publications/silhouettes_human_rec_MVA11.pdf.

Krasin, I., Duerig, T., Alldrin, N., Ferrari, V., Abu-El-Haija, S., Kuznetsova, A., Rom, H., Uijlings, J., Popov, S., Kamali, S., Malloci, M., Pont-Tuset, J., Veit, A., Belongie, S., Gomes, V., Gupta, A., Sun, C., Chechik, G., Cai, D., Feng, Z., Narayanan, D., and Murphy, K., "Openimages: A Public Dataset for Large-Scale Multi-Label and Multi-Class Image Classification," Dataset available from https://storage.googleapis.com/openimages/web/index.html, 2017.

TC2 Labs LLC, "SizeUSA", 3 pages, http://scan2fit.com/sizeusa/about.php.

\* cited by examiner

SLEEP SCORES

BACKGROUND

Many of the existing sleep tracking devices can produce a hypnogram that describes sleep stages during sleep sessions. However, these systems are limited to determining a sleep score based on information such as sleep efficiency, total sleep time, and sleep onset latency, that can be computed from the hypnogram. Existing systems are not able to quantify the hypnogram beyond these discrete aspects.

BRIEF DESCRIPTION OF DRAWINGS

The detailed description is described with reference to the accompanying figures.

DETAILED DESCRIPTION

Described are systems and methods for generating sleep scores based at least in part on the visual appearance of hypnograms, in accordance with described representations. Existing systems may utilize hypnograms to compute factors like sleep efficiency, total sleep time, sleep onset latency, and then utilize that information to generate a sleep score. However, the overall shape of the hypnogram and the various transitions between sleep stages are harder to quantify, yet more accurately represent the overall quality of sleep experienced by the user during a sleep session. To overcome this deficiency in existing systems, the disclosed implementations generate an embedding vector, also referred to herein as an embedding, representative of the visual appearance of a hypnogram and utilize that embedding to determine a sleep score of the sleep session represented by the hypnogram. For example, a deep neural network, such as a convolutional neural network ("CNN"), may be trained with input data that includes hypnograms that have been labeled according to their sleep quality, or sleep score. The trained network may then be provided with an unlabeled hypnogram, generate an embedding representative of that hypnogram, and determine a sleep score corresponding to that hypnogram.

In addition to generating sleep scores based on the visual appearance of a hypnogram, the described implementations may also be utilized to generate and provide one or more recommendations that may be utilized to improve a user's sleep score, thereby improving the user's overall sleep quality. For example, implementations may determine a group of users that are similar to the user and, based on embeddings and sleep scores of those users, determine one or more user behaviors and/or environmental conditions of that group of users to recommend to the user to improve their sleep score. In still other examples, the recommendations may be based in whole or in part on historical information about the user themselves. For example, stored sleep data about the user that corresponds to good sleep scores may be compared to stored or current sleep data of the user that corresponds to poor sleep scores to determine user behavior and/or environmental conditions that are different. Those differences may be identified and provided as recommendations to improve the user's sleep quality and corresponding sleep score.

Figure 1:
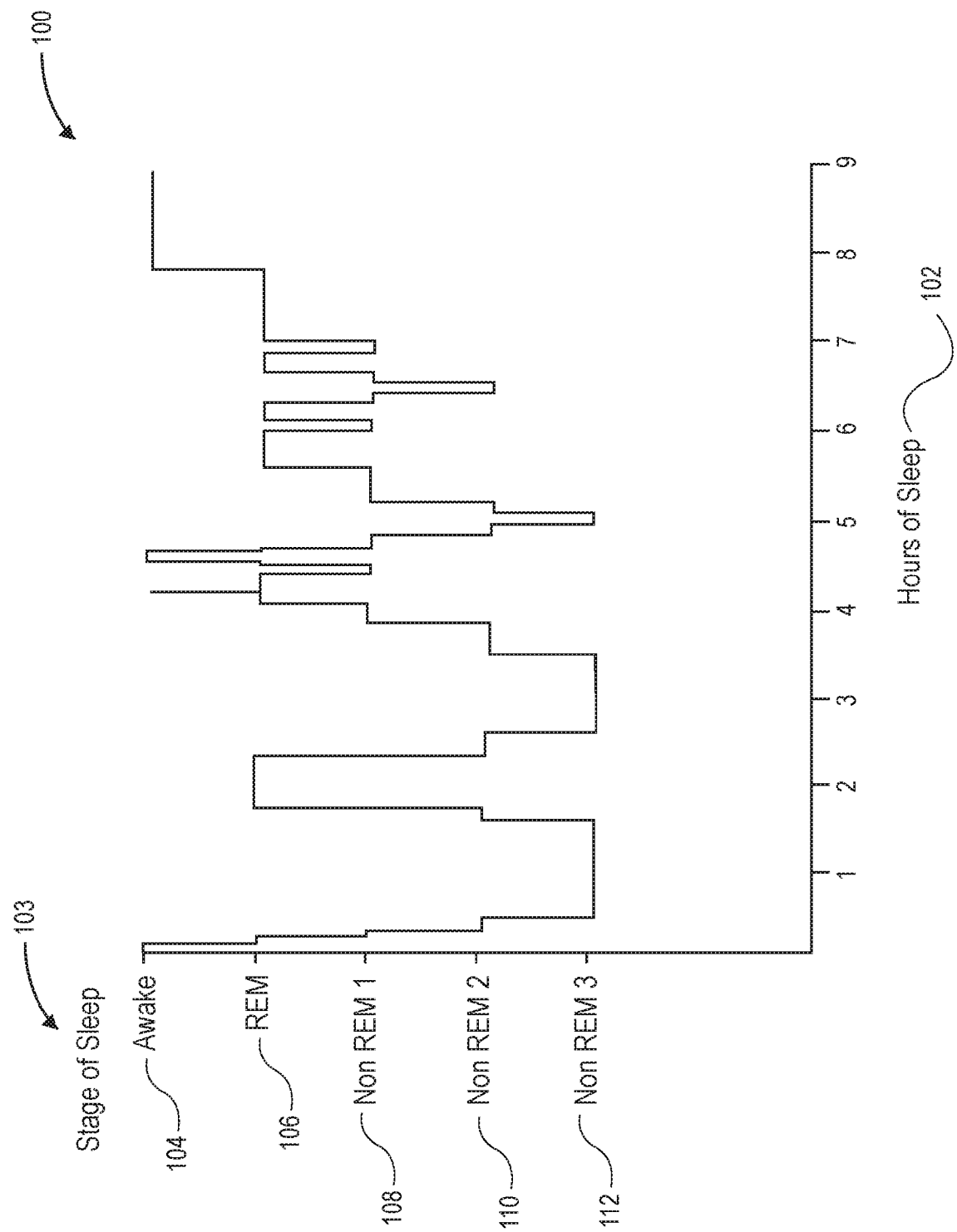
FIG. 1 is an example of a typical hypnogram that may be generated based on user data collected by one or more sensors of a user device during a sleep session of a user, in accordance with described implementations.

FIG. 1 is an example of a typical hypnogram 100 that may be generated based on user data collected by one or more sensors of a user device during a sleep session of a user, in accordance with described implementations.

As illustrated, a hypnogram 100 is a visualization of a number of sleep epochs, which typically represents thirty seconds, during a duration of a sleep session 102 and the corresponding stage of sleep 103 during each epoch. For example, the hypnogram 100 includes four stages of sleep - awake 104, REM 106, non-REM1 108, non-REM2 110, and non-REM3 112. It is worth noting that while the example illustrated in FIG. 1 is a hypnogram showing four stages, in other examples there may be additional stages, such as non-REM4. In other examples, fewer stages may be indicated. For example, in some implementations, non-REM1 and non-REM2 may be group and referred to as a light sleep stage while non-REM3 and non-REM4 may be grouped and referred to as a deep sleep stage. Regardless of the number or grouping of stages, for each epoch during the duration of the sleep session 102, the pixel value of the hypnogram 100 is one of the sleep stages 104 through 112. A typical sleep session of eight hours contains 960 epochs, which can be represented by a 4800 pixel image (960*5 = 4800 pixels).

Figure 2:
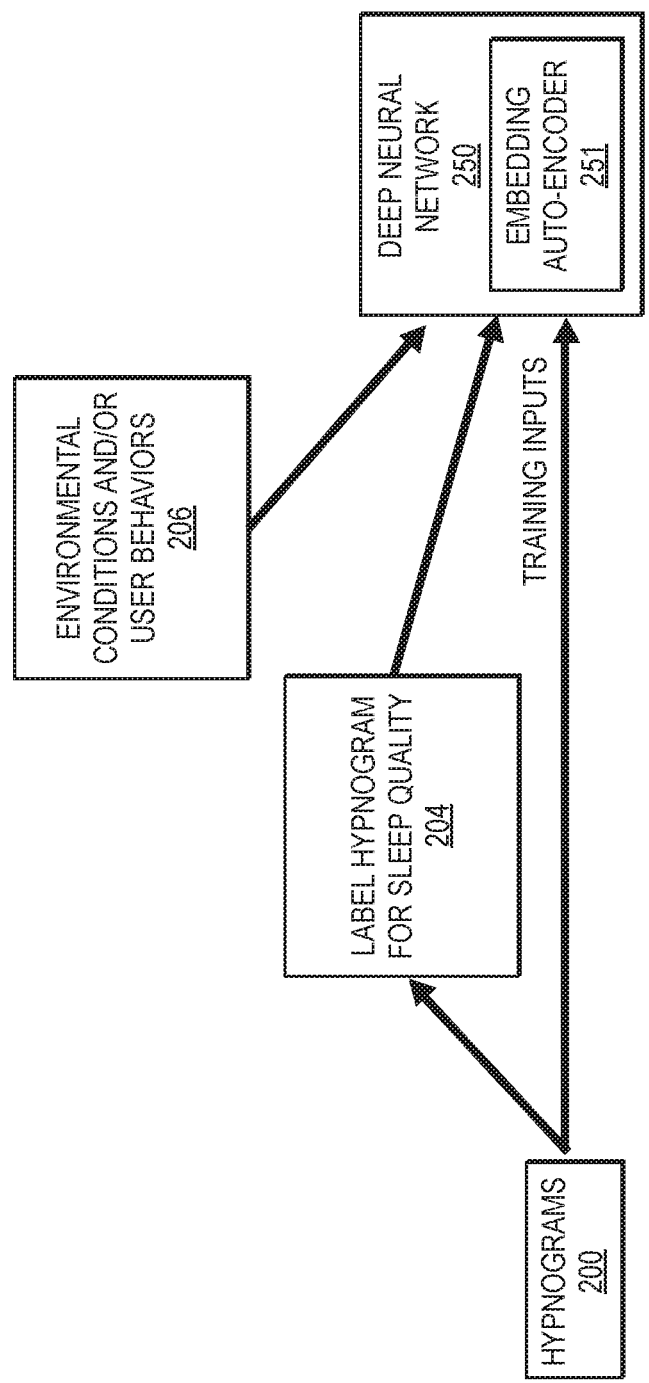
FIG. 2 is a block diagram of an example process for training a deep neural network, such as a convolution neural network, in accordance with described implementations.

FIG. 2 is a block diagram of an example process for training a deep neural network, such as a convolution neural network, in accordance with described implementations.

As illustrated, a set of hypnograms 200 representative of different sleep sessions may be used as the initial training data for the system. The hypnograms may be obtained from any of a variety of sources, such as sleep laboratories, in which case the data may be already labeled by one or more sleep doctors indicating a sleep quality corresponding to the hypnogram. In other examples, hypnograms may be generated from actual user sleep, or simulated using one or more simulation engines. If the input hypnograms have not been labeled, one or more analysts, such as sleep doctors, may label the hypnograms for overall sleep quality 204. Labeling of the hypnograms may consider factors represented by the hypnogram, such as total sleep time ("TST"), time to fall asleep (sleep onset latency), sleep efficiency ("SE"), number and duration of awakenings, the amount of deep and REM sleep, transitions from sleep stage to sleep stage, whether any REM or deep sleep periods were missed, whether the person naturally awoke and from what sleep stage, and/or whether the person attempted to fall back to sleep but could not. Based on these factors, the hypnogram is labeled or scored to indicate the overall quality of sleep represented by the hypnogram.

A sleep score, as used herein, may be any quantitative measure representative of the quality of sleep. For example, sleep scores may be normalized or represented as a percentage. In other examples, sleep scores may be represented on a scale (e.g., 1 to 10). As will be appreciated, any quantitative or qualitative measure or representation may be utilized with the disclosed implementations. Likewise, sleep scores may be grouped and represented in a more simplistic form for user consumption. For example, a sleep score above a defined threshold, referred to herein as a good sleep score threshold, may be associated with "good sleep" and represented to the user as good sleep. For example, a smiley face, green indicator, or other representation may be utilized to convey a good sleep score. Conversely, a score below a defined threshold, referred to herein a poor sleep score threshold, may be associated with "poor sleep" and represented to the user as poor sleep. For example, a frowny face, red indicator, or other representation may be utilized to convey a poor sleep score. Any number or grouping of scores may be utilized. For example, any score above the poor sleep score threshold but below the good sleep score threshold may be classified as "moderate sleep," and represented accordingly.

As will be appreciated, any number of ranges indicative of quality of sleep may be utilized. The disclosed implementations generally discuss three ranges, good sleep, moderate sleep, and poor sleep, along with good sleep scores, moderate sleep scores, and poor sleep scores. These ranges may correspond to any series of scores utilized. For example, if possible sleep scores range between 0% and 100%, the different ranges may be 0% - 33.33% sleep scores corresponding to poor sleep, 33.34% - 66.66% correspond to moderate sleep scores, and 66.67% - 100% correspond to good sleep scores. In other implementations, fewer or additional ranges and corresponding sleep scores may be utilized. Likewise, the ranges may be any grouping of scores and need not be evenly distributed. For example, poor sleep may correspond to any sleep scores between 0% and 50%, moderate sleep may correspond to sleep scores between 50.01% and 75%, and good sleep may correspond to sleep scores between 75.01% and 100%.

The set of hypnograms 200 and the corresponding labels 204 are then provided to a deep neural network 250, such as a CNN for training. In some implementations, environmental conditions and/or user behaviors 206 corresponding to the hypnograms may also be provided as training inputs to the deep neural network 250. The deep neural network 250 generates embeddings based on the visual appearance of each hypnogram. As illustrated, the deep neural network 250 may include an embedding auto-encoder 251 that that generates an embedding vector for each hypnogram. As is known, an embedding may represent the original image with significantly less pixels and the original image can be reconstructed from the embedding, subject to some loss of accuracy. In some instances, the image can be reconstructed with an embedding vector that is 4% to 10% of the number of pixels of the original image. For example, a hypnogram with 4800 pixels (8 hours of sleep) could be represented by an embedding with 192 to 480 pixels.

In this lower dimensional space, the deep neural network is able to determine other similar hypnograms. For example, using a k-nearest neighbors approach, Euclidian distance, or other similar algorithm, the distance between embeddings may be quickly and efficiently determined. As discussed further below, when a non-labeled hypnogram is provided to the trained deep neural network, an embedding is generated, a distance to nearest neighbor embeddings that are labeled/scored is determined, and a sleep score is generated for the non-labeled/scored hypnogram.

Figure 3:
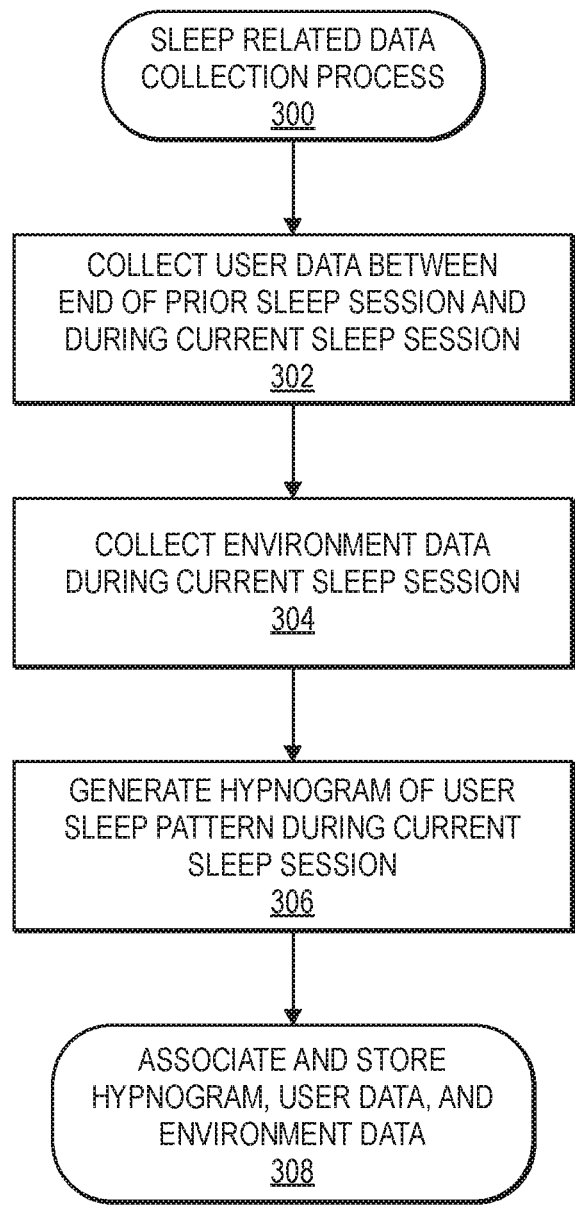
FIG. 3 is an example sleep related data collection process, in accordance with described implementations.
Figure 4:
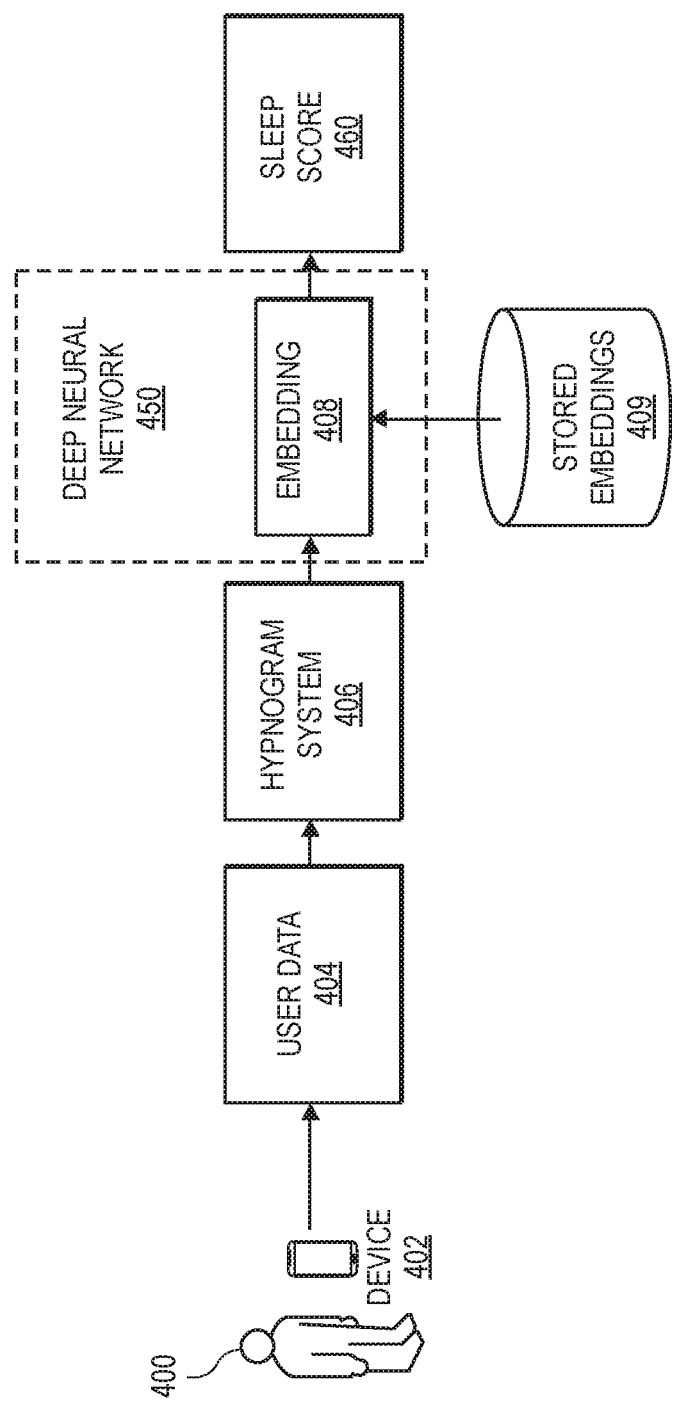
FIG. 4 is a block diagram of an example deep neural network that generates sleep scores, in accordance with described implementations.
Figure 5:
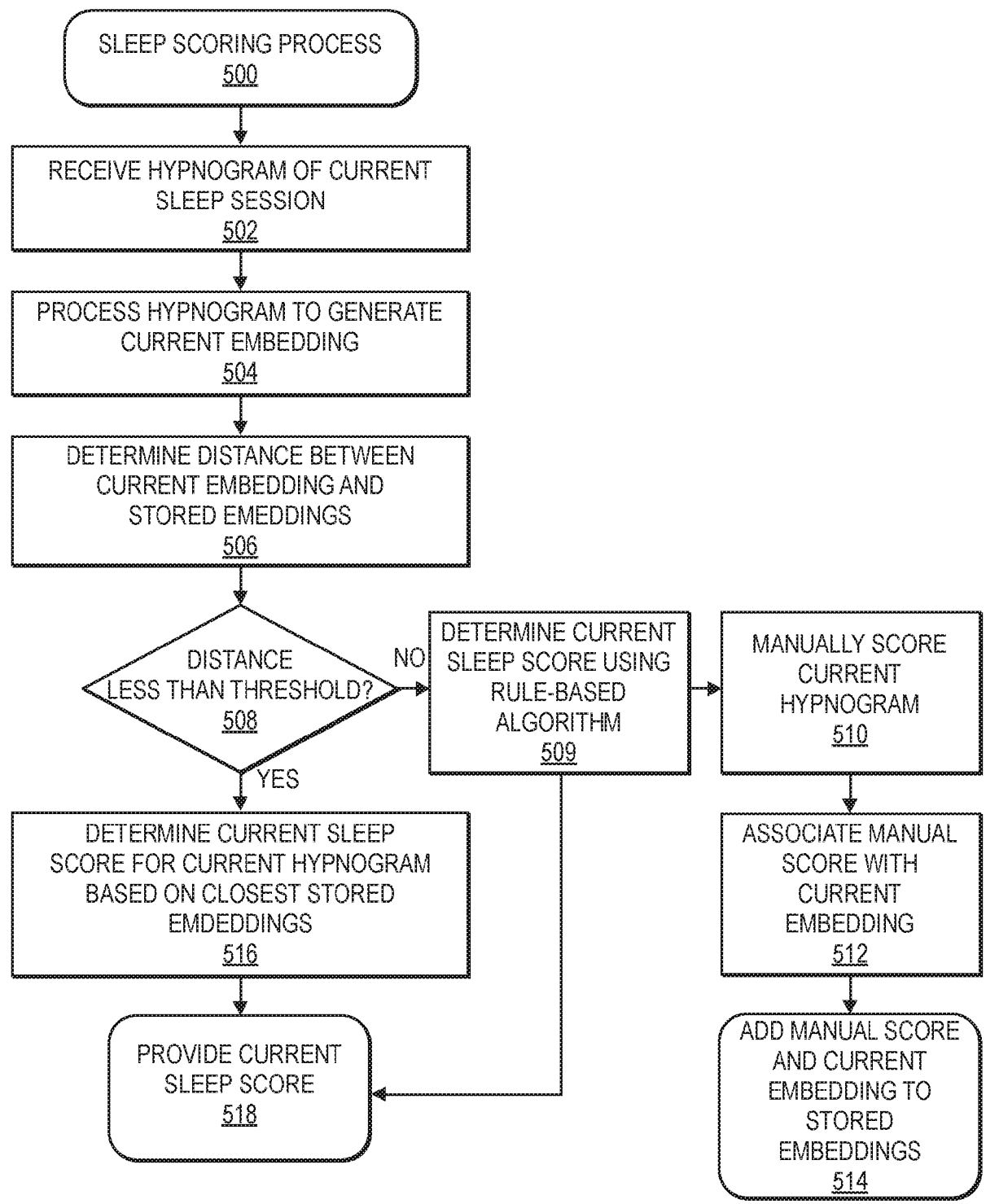
FIG. 5 is an example sleep scoring process, in accordance with described implementations.

FIG. 3 is an example sleep related data collection process 300, in accordance with described implementations.

The example process 300 may be performed in whole or in part by one or more devices, such as a user device worn by a user, or any other device that is operable to collect one or more of environmental data and/or user data. An example user device is discussed in further detail below with respect to FIG. 10.

The example process 300 collects user data between an end of a prior sleep session and during a current sleep session, as in 302. User data may be automatically collected by sensors of one or more devices, such as a wearable, and/or may be provided by a user, for example through an application executing on a user device. For example, sensors may be used to automatically collect user data such as, but not limited to, heartrate, body temperature, movement, perspiration rate, respiration rate, activity or movement, body weight, age, gender, body mass, SpO2, heart rate variability, etc. In some implementations, only some of the scores may be computed and used to generate a sleep score. In still other implementations, the score of the nearest neighbor stored embedding, even though beyond the threshold, may be presented to the user to provide the user with an immediate score.

In addition to either generating a rule based score or providing the score from the nearest neighbor stored embedding, the current hypnogram may be provided to one or more analysts, such as sleep specialists or sleep doctors and those one or more analysts may manually assign a sleep score to the hypnogram, as in 510. The manually determined sleep score may then be associated with the embedding generated for the hypnogram, as in 512, and the embedding and associated sleep score added to the stored embeddings for use in scoring of future embeddings that are received by the example process 500, as in 514.

Returning to decision block 508, if it is determined that the distance does not exceed the threshold - i.e., that the similarity between the embedding and the nearest neighbor is high, a current score for the current hypnogram is determined based on the score of the determined nearest neighbor stored embedding(s), as in 516. In one implementation, the current score may be the same score as the score associated with the determined nearest neighbor embedding. In other examples, the current score may be an average or weighted average of sleep scores associated with a plurality of determined nearest neighbors, or an average of the sleep scores associated with nearest neighbor embeddings that are within a defined distance of the current embedding.

Finally, after computing the current sleep score in block 516 based on the score(s) associated with nearest neighbor stored embeddings or determining a sleep score in block 509, the computed/determined current sleep score is provided to the user as an indicator of the quality of sleep experienced by the user during the current sleep session, as in 518. For example, the sleep score may be presented to the user through one or more computing programs or applications executing on a user device of the user.

Figure 6:
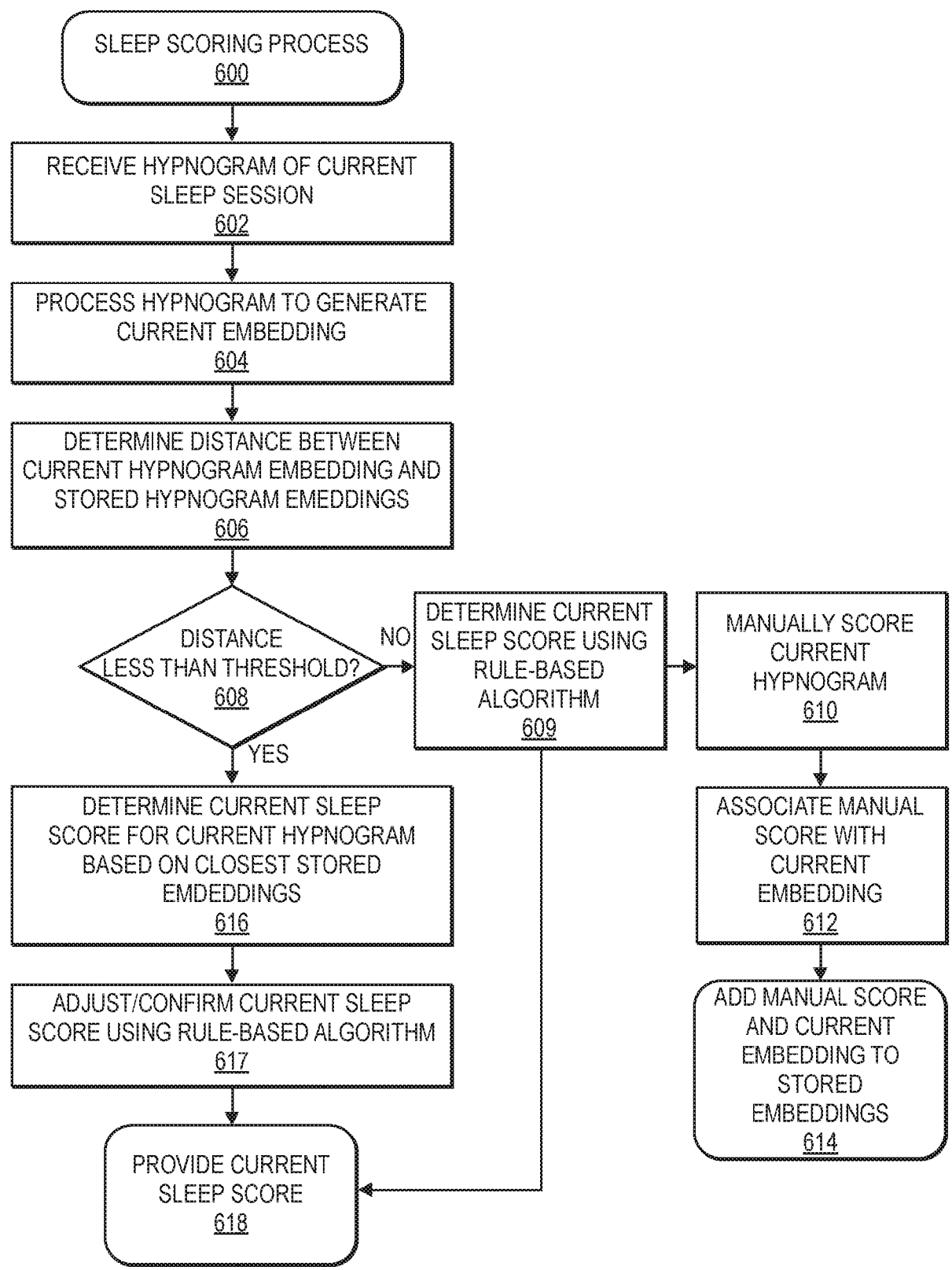
FIG. 6 is another example sleep scoring process, in accordance with described implementations.

FIG. 6 is another example sleep scoring process 600, in accordance with described implementations.

The example process 600 begins upon receipt of a hypnogram of a current sleep session of a user, as in 602. As discussed above, a hypnogram may be generated from user data collected during the sleep session. In other implementations, the hypnogram may be received from another source. For example, the hypnogram may be provided or received from a third party, such as sleep lab that generated the hypnogram for a user during the user sleep session.

Regardless of the source of the hypnogram, the example process 600 generates an embedding vector from the image of the received current hypnogram, as in 604. As discussed above, the embedding vector may be generated by a deep neural network, such as a trained CNN. The example process 600 then determines one or more stored and labeled embeddings that are closest in similarity to the current embedding vector, as in 606. For example, a nearest neighbors algorithm, such as k-nearest neighbors, Euclidian distance, etc., may be utilized to determine a distance between the current embedding and stored embeddings that are labeled/scored. The stored embedding(s) with the shortest distance may be determined to have the highest similarity with the current embedding.

In some implementations, a determination may then be made as to whether the distance or similarity between the current embedding and the stored embeddings exceeds a threshold, as in 608. For example, if the similarity is based on the distance computed between the embeddings, it may be determined if the computed distance is less than a threshold - the shorter the distance the more similar the two embeddings. The threshold may be any value or indicator and may vary for different embeddings, different users, different hypnograms, etc.

If it is determined that the distance between the embedding and the nearest neighbor is not less than the threshold, a current sleep score may be computed using a traditional approach, such as a rule-based algorithm, so that a result can be quickly returned to the user, as in 609. A traditional rule-based algorithm may, for example, compute scores for one or more of TST, SE, sleep onset latency, percentage of deep sleep time, percentage of REM sleep time, wakefulness after falling asleep ("WASO") duration, and/or number of awakenings during the sleep session, and then combine those scores to compute a sleep score for the sleep session. TST, SE, sleep onset latency, percentage of deep sleep time, percentage of REM sleep time, WASO, and number of awakenings may be computed from a hypnogram using known techniques that need not be discussed further in detail herein. In other implementations, the score of the nearest neighbor stored embedding, even though beyond the threshold, may be presented to the user to provide the user with an immediate score.

In addition to either generating a rule based score or providing the score from the nearest neighbor stored embedding, the current hypnogram may be provided to one or more analysts, such as sleep specialists or sleep doctors and those one or more analysts may manually assign a sleep score to the hypnogram, as in 610. The manually determined sleep score may then be associated with the embedding generated for the hypnogram, as in 612, and the embedding and associated sleep score added to the stored embeddings for use in scoring of future embeddings that are received by the example process 600, as in 614. This active learning enables continual updates of the system as new embeddings are identified such that they can be used to compute sleeps scores for other future embeddings.

Returning to decision block 608, if it is determined that the distance does not exceed the threshold - i.e., that the similarity between the embedding and the nearest neighbor is high, a current score for the current hypnogram is determined based on the score of the determined nearest neighbor stored embedding(s), as in 616. In one implementation, the current score may be the same score as the score associated with the determined nearest neighbor embedding. In other examples, the current score may be an average or weighted average of sleep scores associated with a plurality of determined nearest neighbors, or an average of the sleep scores associated with nearest neighbor embeddings that are within a defined distance of the current embedding. In another example, embeddings may be grouped into buckets or sets and a sets a group or set of embeddings that are closest in distance to the current embedding may be used to determine the current sleep score.

In this example, the current sleep score determined at block 616 may be adjusted based on one or more rule-based algorithms, as in 617. As discussed above, a traditional rule-based algorithm may, for example, compute scores for one or more of TST, SE, sleep onset latency, percentage of deep sleep time, percentage of REM sleep time, WASO, number of awakenings during the sleep session, etc. In this example process 600, one or more of those scores may be utilized to increase or decrease the current sleep score. Alternatively, one or more of the scores may be used to confirm that the current sleep score is within an expected range.

Finally, after computing the current sleep score in block 616 based on the score(s) associated with nearest neighbor stored embeddings and optionally adjusting that score based on one or more rule-based algorithms, in block 617, or determining a sleep score in block 609, the computed/determined current sleep score is provided to the user as an indicator of the quality of sleep experienced by the user during the current sleep session, as in 618. For example, the sleep score may be presented to the user through one or more computing programs or applications executing on a user device of the user.

Figure 7:
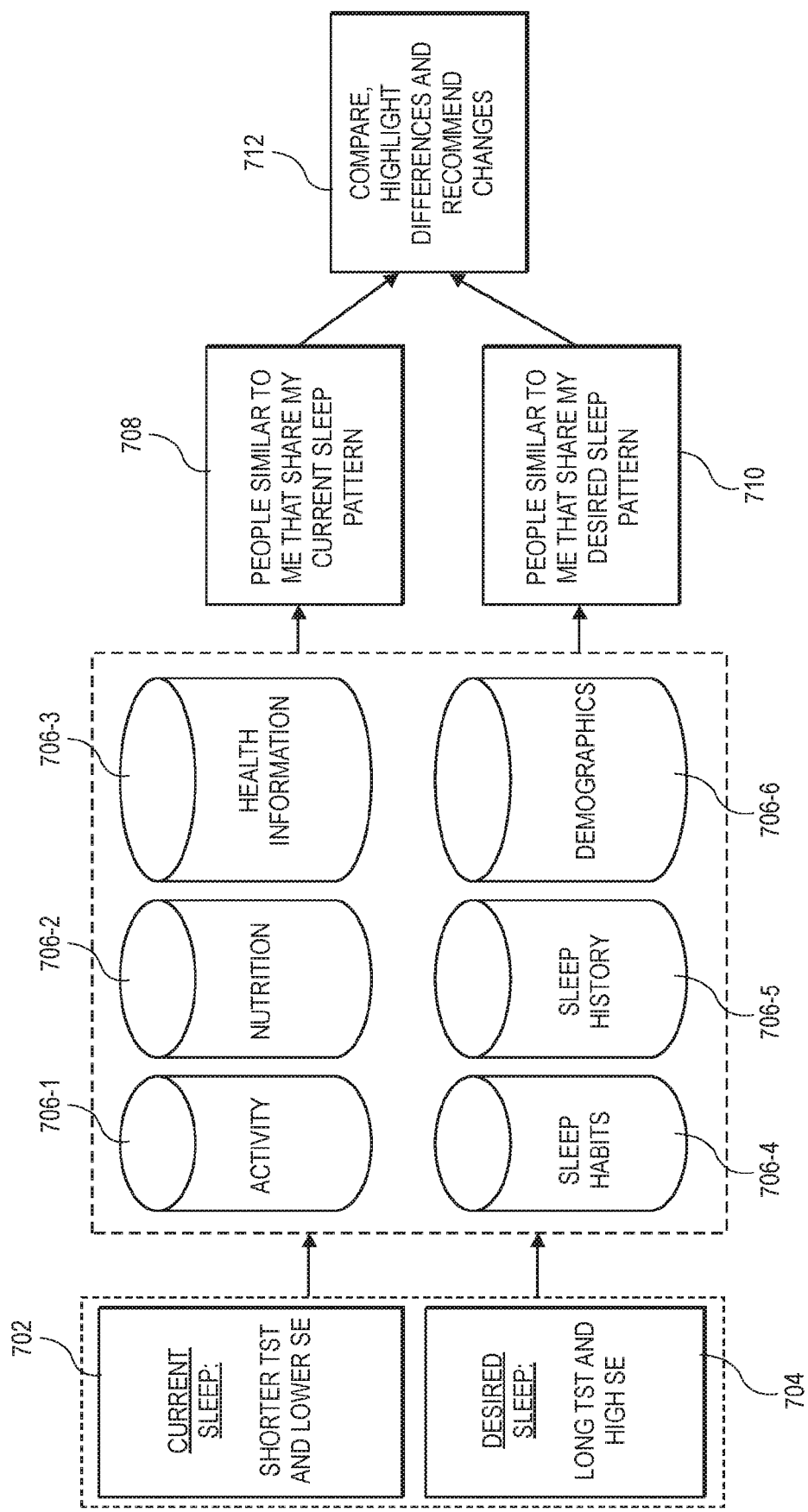
FIG. 7 is a block diagram of an example system for generating recommended changes to improve a sleep score, in accordance with described implementations.

FIG. 7 is a block diagram of an example system for generating recommended changes to improve a sleep score, in accordance with described implementations.

As discussed above, a current sleep score 702 for a user may be determined using the described implementations. In this example, the current sleep score 702 is representative of poor sleep quality that includes a shorter total sleep time (e.g., five hours) and poor sleep efficiency. Likewise, a user may specify or select a desired sleep score 704. Alternatively, the disclosed implementations may indicate or suggest a desired sleep score, which may correspond to good sleep versus poor sleep. Alternatively, if a user currently has a poor sleep score, the disclosed implementation mays take a more step-wise approach and suggest a desired sleep score that corresponds to moderate sleep quality. If/when the user reaches a moderate sleep score, the system may then suggest a good sleep quality score. Such a step wise fashion may be more conducive to a user and not as overwhelming when recommended changes are suggested.

To determine recommended changes in the user behavior or environmental conditions that may help the user improve their sleep score and corresponding quality of sleep, user data 706 such as user activity 706-1, nutrition 706-2, health information 706-3, sleep habits 706-4, sleep history 706-5, demographics 706-6, etc., may be maintained for a plurality of users. Users of the disclosed implementations may elect or specify what, if any information is maintained by the disclosed implementations and used to identify other similar users and/or determine recommended changes.

Stored user information, such as those listed above and illustrated in FIG. 7, may be used to determine other users that are similar to the current user. For example, a second plurality of the plurality of users that have similar demographics 706-6, health 706-3, nutrition 706-2, activity level 706-1, etc., to the current user may be determined based on the user data 706. For that second plurality of users, a first subset of users 710 with hypnograms corresponding to the desired sleep quality 704 may be identified. Likewise, a second subset of users 708 from the second plurality of users with hypnograms corresponding to the users current sleep score 702 may be identified. For example, the embedding vector corresponding to the user's current hypnogram may be compared to embeddings of stored hypnograms for the first plurality of users to determine the second subset of users 710 with similar hypnograms and thus similar sleep scores. Likewise, an embedding representative of a hypnogram corresponding to the desired sleep score may be determined and compared with stored embeddings of second plurality of users to determine the first subset of users 708 with hypnograms corresponding to the desired sleep score.

Similarities in user behavior and/or environmental conditions between the first subset of users 710 may be determined and indicated as factors that may correspond to good sleep. Likewise, similarities in user behavior and/or environmental conditions between the second subset of users 708 may be determined as indicated as factors that may correspond to poor sleep. Finally, differences 712 between the good factors and the poor factors may be determined and recommended as changes to improve the user's quality of sleep. For example, if a majority of the first subset of users 710 read quietly for thirty minutes before starting a sleep session and a majority of the second subset of users 708 watch television or interact with a computer for thirty minutes or more before starting a sleep session, the disclosed implementations may determine these differences and recommend that the user start reading for thirty minutes before starting a sleep session and stop watching television or interacting with computing devices during those thirty minutes.

Figure 8:
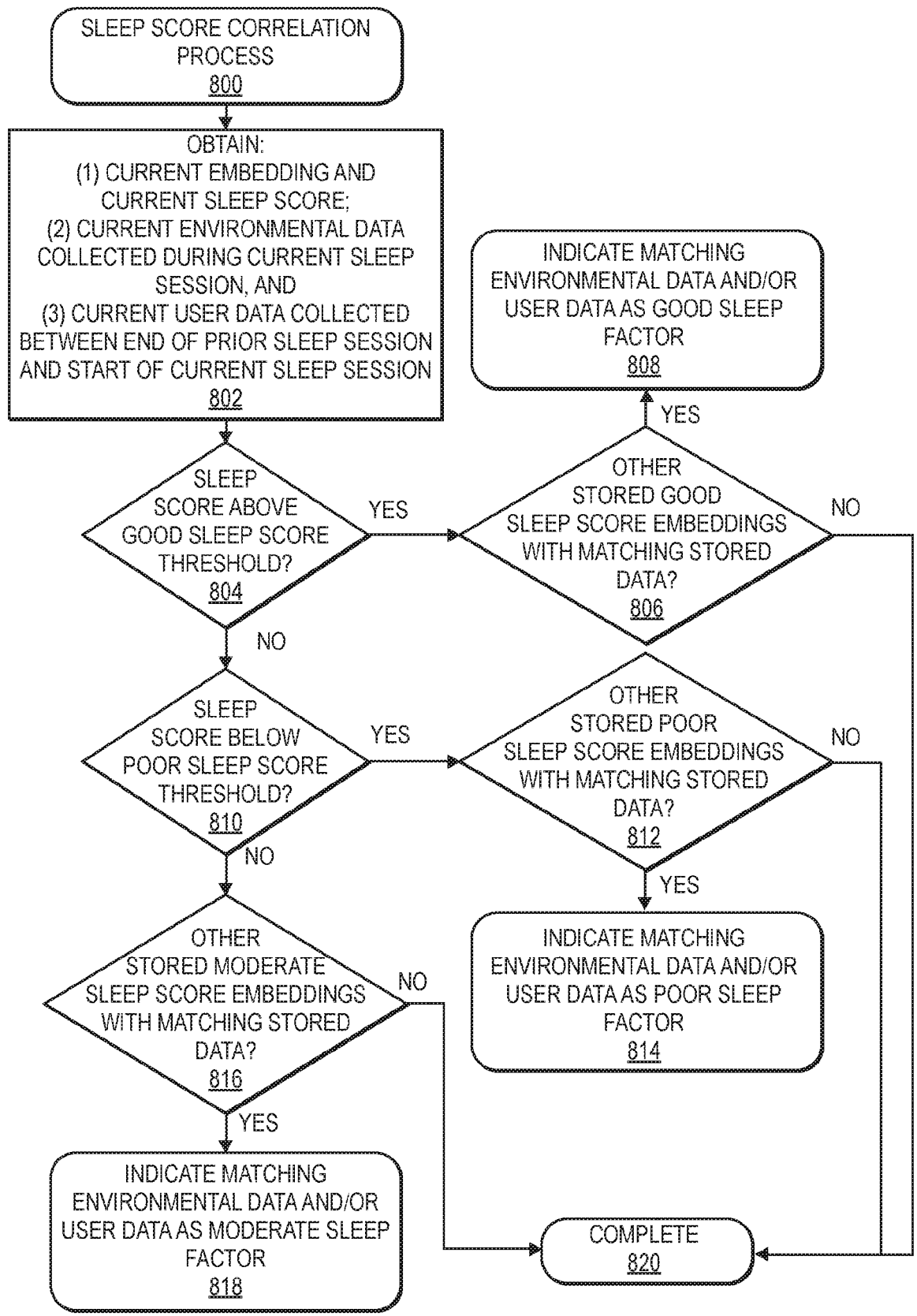
FIG. 8 is an example sleep score correlation process, in accordance with described implementations.

FIG. 8 is an example sleep score correlation process 800, in accordance with described implementations.

The example process 800 begins by obtaining or receiving a current embedding and current sleep score of a user, current environmental data collecting during the current sleep session, and current user data collected between the end of a prior sleep session and a start of the current sleep session, as in 802.

A determination may then be made as to whether the user's current sleep score is above a good sleep score threshold, as in 804. A good sleep score threshold may be any value or indicator of good sleep and may be different for different users, different age groups, different genders, etc. In some implementations, a user may specify what constitutes a good sleep score value.

If it is determined that the current sleep score is above the good sleep score threshold, it is determined whether other stored good sleep score embeddings exist with matching stored data, as in 806. For example, the current embedding may be compared with stored embeddings of other users and/or stored embeddings of the same user generated at prior points in time to determine those with matching data.

Similar to computing a sleep score, similar embeddings of hypnograms of users may be determined by computing a distance, for example using k-nearest neighbors algorithm, Euclidian distance, etc., between the current embedding of the user and stored embeddings of other users and/or stored embeddings of the same user generated at prior points in time. For those embeddings that are determined to be similar, it may further be determined which of those embeddings have similar or matching user data and/or environmental conditions. In some implementations, this comparison may be limited to embeddings of hypnograms of users that are determined to be similar to the current user. In other implementations, user data and/or environmental conditions for any users having similar embeddings may be utilized.

Matching environmental data and/or user data present in a majority of the embeddings determined to be similar to the current embedding are indicated as good sleep factors, as in 808.

Returning to block 804, if it is determined that the sleep score is not above a good sleep threshold, it is determined whether the current sleep score is below a poor sleep threshold, as in 810. Similar to a good sleep score threshold, a poor sleep score threshold may be any value or indicator of poor sleep and may be different for different users, different age groups, different genders, etc. In some implementations, a user may specify what constitutes a poor sleep score value.

If it is determined that the current sleep score is below the poor sleep score threshold, it is determined whether other stored poor sleep score embeddings exist with matching stored data, as in 812. For example, the current embedding may be compared with stored embeddings of other users and/or stored embeddings of the same user generated at prior points in time to determine those that are similar.

Similar to computing a sleep score, similar embeddings of hypnograms of users may be determined by computing a distance, for example using k-nearest neighbors algorithm, Euclidian distance, etc., between the current embedding of the user and stored embeddings of other users and/or stored embeddings of the same user generated at prior points in time. For those embeddings that are determined to be similar, it may further be determined which of those embeddings have similar or matching user data and/or environmental conditions. In some implementations, this comparison may be limited to embeddings of hypnograms of users that are determined to be similar to the current user. In other implementations, user data and/or environmental conditions for any users having similar embeddings may be utilized.

Matching environmental data and/or user data present in a majority of the embeddings determined to be similar to the current embedding are indicated as poor sleep factors, as in 814.

Returning to block 810, if it is determined that the sleep score is not below the poor sleep score threshold, it is determined whether other stored moderate sleep score embeddings exist with matching stored data, as in 816. For example, the current embedding may be compared with stored embeddings of other users and/or stored embeddings of the same user generated at prior points in time to determine those that are similar.

Similar to computing a sleep score, similar embeddings of hypnograms of users may be determined by computing a distance, for example using k-nearest neighbors algorithm, Euclidian distance, etc., between the current embedding of the user and stored embeddings of other users and/or stored embeddings of the same user generated at prior points in time. For those embeddings that are determined to be similar, it may further be determined which of those embeddings have similar or matching user data and/or environmental conditions. In some implementations, this comparison may be limited to embeddings of hypnograms of users that are determined to be similar to the current user. In other implementations, user data and/or environmental conditions for any users having similar embeddings may be utilized.

Matching environmental data and/or user data present in a majority of the embeddings determined to be similar to the current embedding are indicated moderate sleep factors, as in 818.

Finally, if it is determined that there are no other stored embeddings with good sleep score, poor sleep scores, or moderate sleep scores that include matching data, the example process completes, as in 820.

Figure 9A:
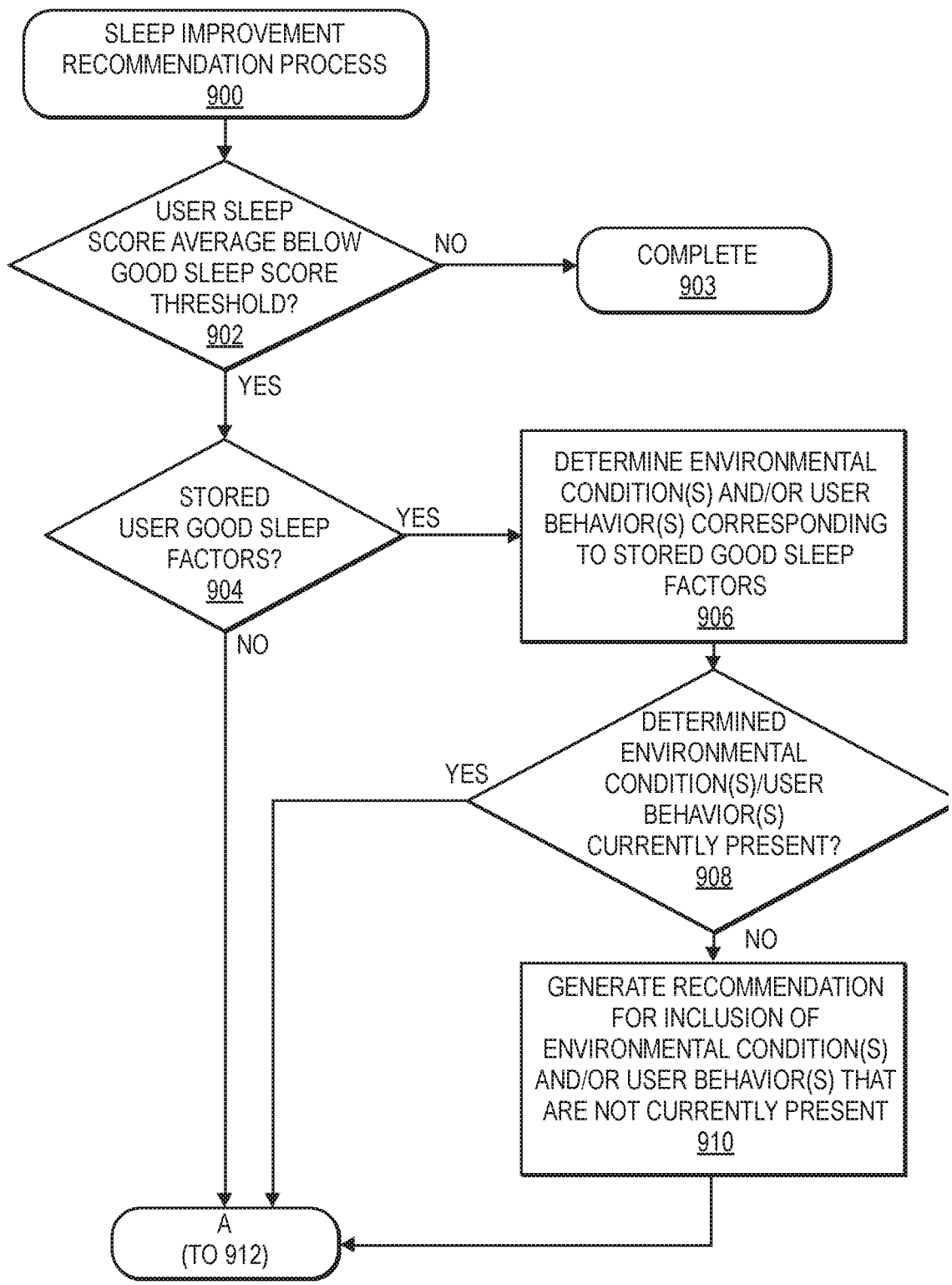
FIG. 9A though 9C are an example sleep improvement recommendation process, in accordance with described implementations.

FIGS. 9A *though* 9C are an example sleep improvement recommendation process 900, in accordance with described implementations.

The example process 900 begins by determining if the user sleep score or sleep score average is below the good sleep score threshold, as in 902. If it is determined that the users sleep score average is not below the good sleep score threshold, the example process 900 completes, as in 903.

However, if it is determined that the user sleep score or sleep score average is below the good sleep score threshold, a determination is made as to whether there are stored good sleep factors that have been previously determined from hypnograms of prior sleep sessions of the user, as in 904. An example process for indicating good sleep factors for a user are discussed above with respect to FIG. 8. If there are stored user good sleep factors, environmental conditions and/or user behaviors corresponding to the stored user good sleep factors are determined, as in 906. In addition, a determination is made as to whether those environmental conditions and/or user behaviors corresponding to the stored user good sleep factors are currently present environmental conditions and/or user behaviors of the user, as in 908. As discussed above, environmental conditions and/or user behavior may be collected and associated with hypnograms generated for each user sleep session. The stored user environmental conditions and/or user behaviors corresponding to stored user good sleep factors may be compared with current user environmental conditions and/or current user behaviors to determine if those conditions/behaviors are currently present for the user.

If it is determined that one or more of the environmental conditions and/or user behaviors corresponding to the stored user good sleep factors are not currently present for the user, a recommendation may be generated for inclusion of the environmental condition and/or user behaviors that are not currently present for the user, as in 910.

Figure 9B:
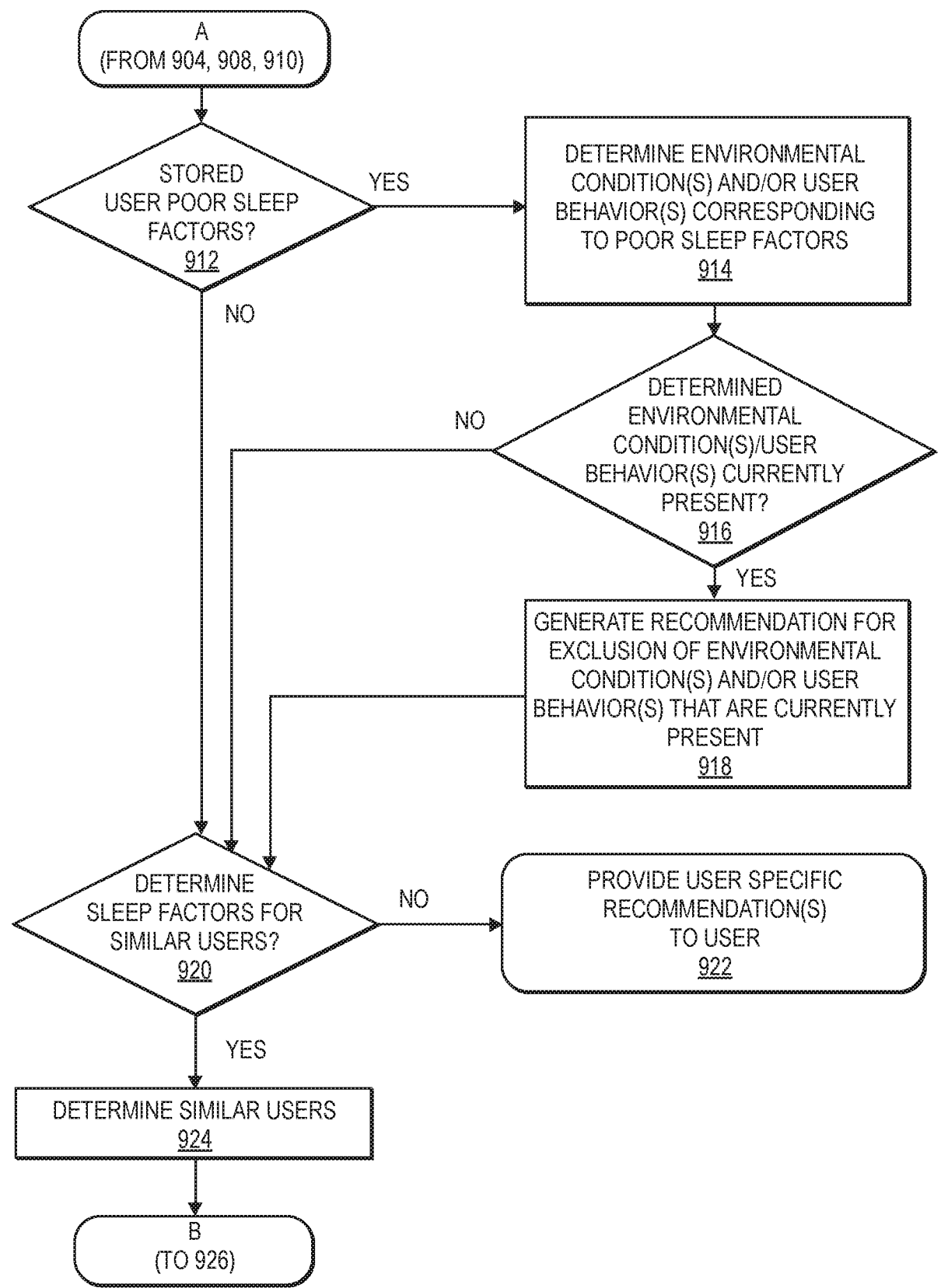

Referring now to FIG. 9B, it if is determined at decision block 904 that there are no stored user good sleep factors, or if it is determined at decision block 908 that the environmental conditions and/or user behaviors corresponds to stored user good sleep factors are already present for the user, or recommendations are generated in block 910, a determination is made as to whether there are stored user poor sleep factors, as in 912. Poor sleep factors may be determined and stored as discussed above with respect to FIG. 8.

If there are stored user poor sleep factors, environmental conditions and/or user behaviors corresponding to the stored user poor sleep factors are determined, as in 914. In addition, a determination is made as to whether those environmental conditions and/or user behaviors corresponding to the stored user poor sleep factors are currently present environmental conditions and/or user behaviors of the user, as in 916. As discussed above, environmental conditions and/or user behavior may be collected and associated with hypnograms generated for each user sleep session. The stored user environmental conditions and/or user behaviors corresponding to stored user poor sleep factors may be compared with current user environmental conditions and/or current user behaviors to determine if those conditions/behaviors are currently present for the user.

If it is determined that one or more of the environmental conditions and/or user behaviors corresponding to the stored user poor sleep factors are currently present for the user, a recommendation may be generated for exclusion of the environmental condition and/or user behaviors that are not currently present for the user, as in 918.

By comparing current environmental conditions and/or user behaviors of the user with stored environmental conditions and/or user behaviors of the same user corresponding to prior sleep sessions, a direct correlation may be made as to sleep factors that may improve the sleep score of the user and/or sleep factors that may detract from the sleep score of the user.

In some implementations it may also be determined whether sleep factors for other, similar users are to be considered, as in 920. If it is determined that sleep factors for other users are not to be considered, the example process provides some or all of the user specific recommendations generated at blocks 910 and 918 to the user as recommended changes to improve the user's sleep score and resultant quality of sleep, as in 922.

If it is determined that sleep factors are to be determined for other users, other users that are similar to the current user are determined, as in 924. Other similar users may be determined based on any of a variety of factors including, but not limited to, age, gender, race, demographics, weight, stress level, activity level, etc.

Figure 9C:
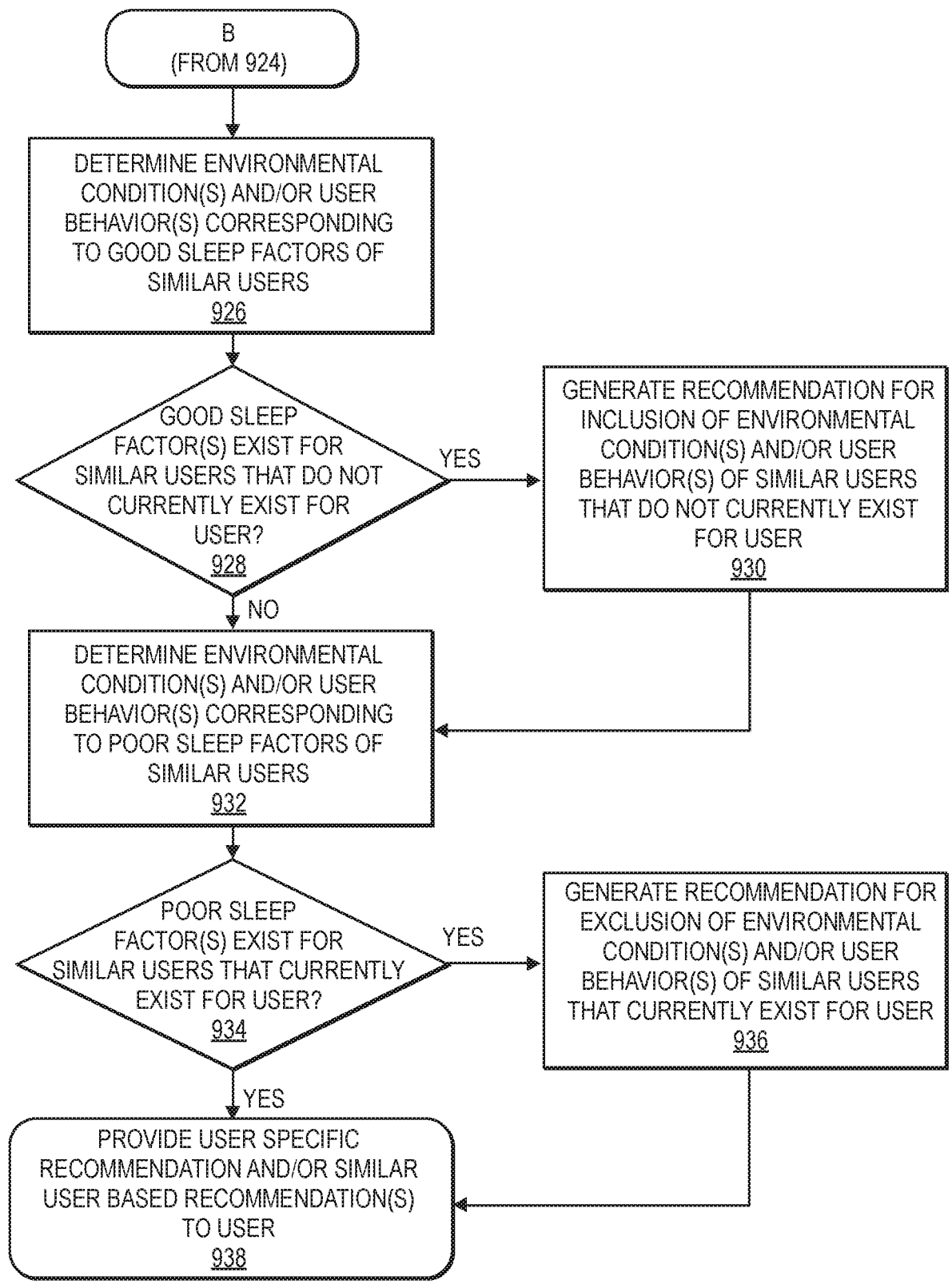

Referring now to FIG. 9C, for the determined similar users, environmental conditions and/or user corresponding to good sleep factors of those users are determined or obtained, as in 926. Generation of good sleep factors is discussed above with respect to FIG. 8.

A determination may then be made as to whether good sleep factors exist for similar users that do not currently exist for the user, as in 928. If it is determined that there are good sleep factors that exist for the other users that do not currently exist for the user, recommendations for inclusion of environmental conditions and/or user data corresponding to those good sleep factors are generated, as in 930.

After generating inclusion recommendations at block 930, or if it is determined at decision block 928 that good sleep factors do not exist for similar users that do not also currently exist for the user, environmental conditions and/or user behaviors corresponding to poor sleep factors of similar users are determined, as in 932.

A determination is then made as to whether poor sleep factors exist for similar users that also currently exist for the user, as in 934. If it is determined that there are poor sleep factors that exist for the similar users that also currently exist for the user, recommendations for exclusion of the environmental conditions and/or user behaviors correspond to those poor sleep factors that exist for the similar users and currently exist for the user are generated, as in 936.

Finally, some or all of the user specific recommendations generated in blocks 910 and/or 918, and/or the similar user based recommendations generated in blocks 930 and 936 are sent for presentation to a user as recommended changes to improve the user sleep score and corresponding sleep quality, as in 938.

Figure 10:
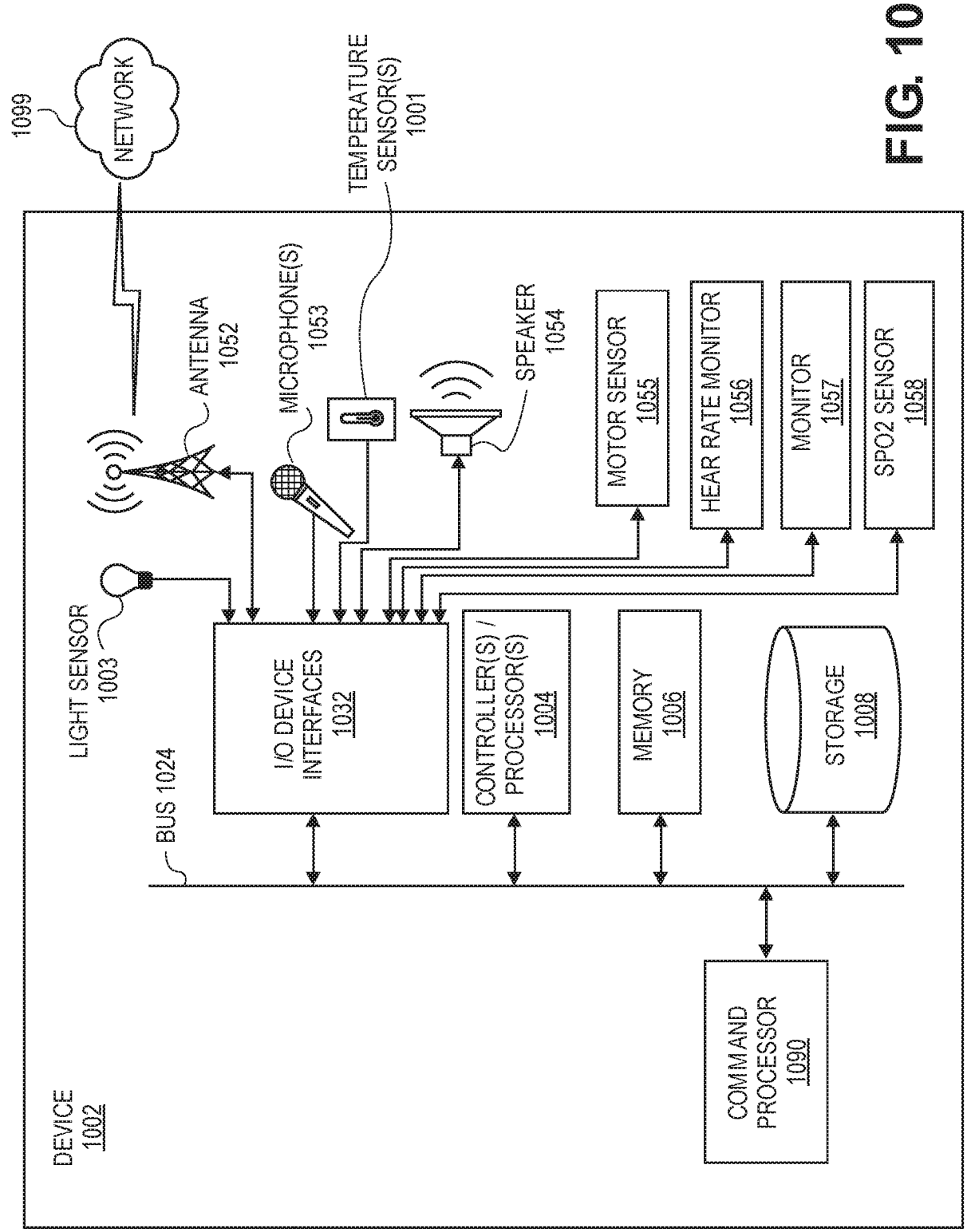
FIG. 10 illustrates example components of a user device, in accordance with described implementations.
Figure 11:
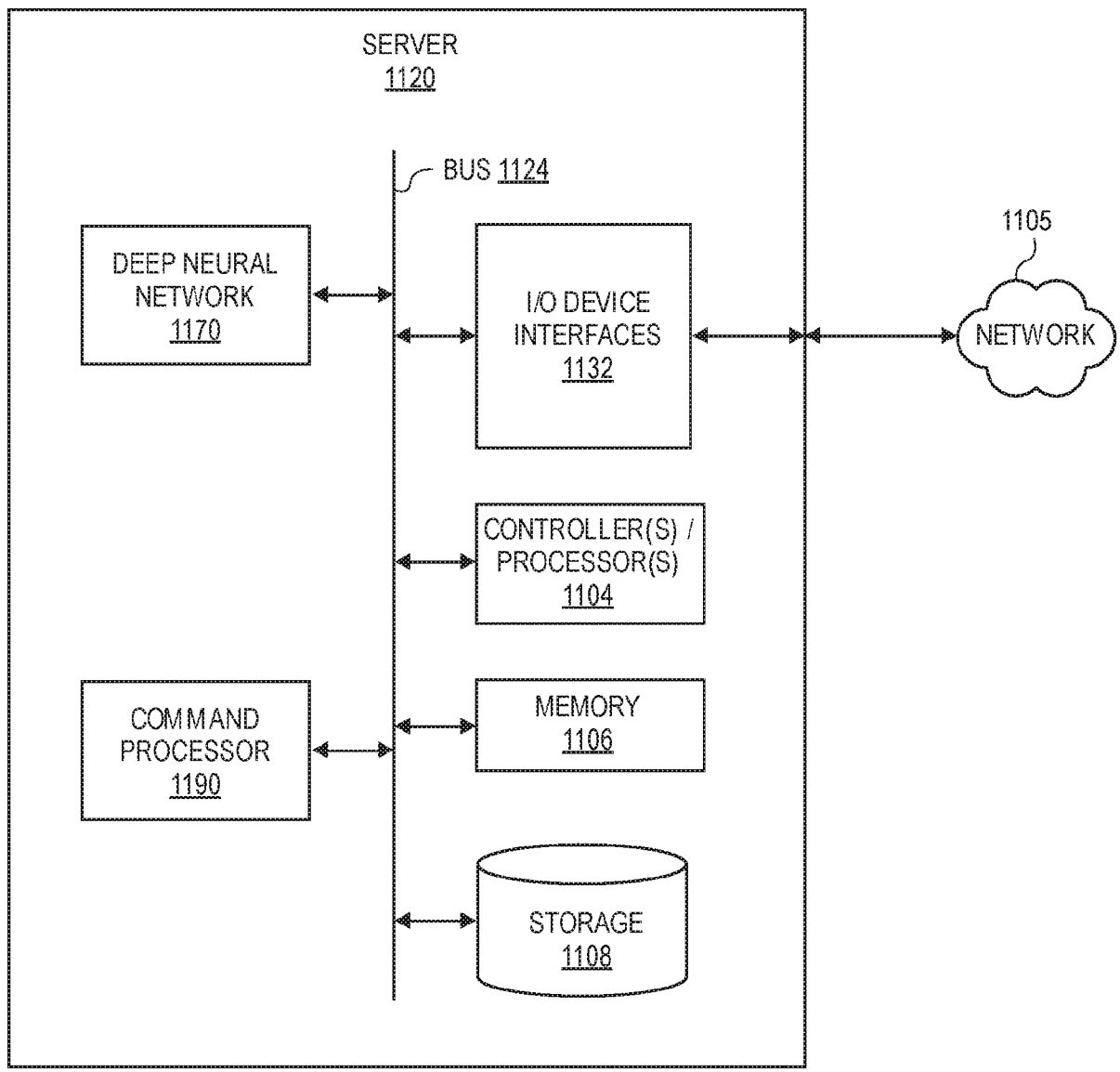
FIG. 11 illustrates example components of a server, in accordance with described implementations.

FIG. 10 is a block diagram conceptually illustrating a user device 1002 that may be used with the described implementations. FIG. 11 is a block diagram conceptually illustrating example components of a remote computing device, such as a remote server 1120 that may assist with sleep quality scoring and/or generating sleep recommendations, in accordance with described implementations. Multiple such servers 1120 may be included in the system, such as one server(s) 1120 for generating a hypnogram from user data received from the user device 1002, one server(s) for generating an embedding from the hypnogram, one server(s) for the trained neural network that determines a sleep score based on the embedding, user data and/or environmental data, etc. In operation, each of these devices (or groups of devices) may include computer-readable and computer-executable instructions that reside on the respective device (1002/1120), as will be discussed further below.

Each of these devices (1002/1120) may include one or more controllers/processors (1004/1104), that may each include a central processing unit (CPU) for processing data and computer-readable instructions, and a memory (1006/1106) for storing data and instructions of the respective device. The memories (1006/1106) may individually include volatile random access memory (RAM), non-volatile read only memory (ROM), non-volatile magnetoresistive (MRAM) and/or other types of memory. Each device may also include a data storage component (1008/1108), for storing data, controller/processor-executable instructions, sets of stored embeddings, and/or associations between sleep scores and embeddings. Each data storage component may individually include one or more non-volatile storage types such as magnetic storage, optical storage, solid-state storage, etc. Each device may also be connected to removable or external non-volatile memory and/or storage (such as a removable memory card, memory key drive, networked storage, etc.) through respective input/output device interfaces (1032/1132).

Computer instructions for operating each device (1002/1120) and its various components may be executed by the respective device's controller(s)/processor(s) (1004/1104), using the memory (1006/1106) as temporary "working" storage at runtime. A device's computer instructions may be stored in a non-transitory manner in non-volatile memory (1006/1106), storage (1008/1108), or an external device(s). Alternatively, some or all of the executable instructions may be embedded in hardware or firmware on the respective device in addition to or instead of software.

Each device (1002/1120) includes input/output device interfaces (1032/1132). A variety of components may be connected through the input/output device interfaces. Additionally, each device (1002/1120) may include an address/data bus (1024/1124) for conveying data among components of the respective device. Each component within a device (1002/1120) may also be directly connected to other components in addition to (or instead of) being connected to other components across the bus (1024/1124).

Referring to the device 1002 of FIG. 10, the device 1002 may be "headless" and may primarily rely on spoken commands for input and/or through interaction with one or more control interfaces or buttons. In other examples, the device 1002 may include a display, which may allow a touch-based interface. The device 1002 may also include input/output device interfaces 1032 that connect to a variety of components such as an audio output component such as a speaker 1054, a wired headset or a wireless headset, and/or other components capable of outputting audio. The device 1002 may also include an audio capture component. The audio capture component may be, for example, a microphone 1053 or array of microphones, a wired headset or a wireless headset, etc. The microphone 1053 may be configured to capture audio, such as environmental noises. If an array of microphones is included, approximate distance to a sound's point of origin may be determined using, for example, acoustic localization based on time and amplitude differences between sounds captured by different microphones of the array.

The device 1002 may also include other sensors that collect sensor data that may be representative of user data and/or environment data. Any number and/or type of sensors may be included in the device. In the illustrated example, in addition to the microphone, the device 1002 includes a light sensor 1003 that may measure the ambient light, one or more temperature sensors 1001 that may measure the ambient temperature and/or measure the temperature of the user. In addition, the device 1002 may include a motion sensor 1055, such as an accelerometer, gyroscope, etc., to measure movement of the user, a heartrate monitor 1056 to measure the heartrate of the user, an SpO2 sensor 1058 to measure the saturation percentage of oxygen in the blood, and/or other sensors/monitors 1057 to measure other user data and/or environment data.

The device may also include a communication interface, such as an antenna 1052. Any form of wired and/or wireless communication may be utilized to facilitate communication between the device 1002 and other devices. For example, any one or more of 802.15.4 (ZIGBEE), 802.11 (WI-FI), 802.16 (WiMAX), BLUETOOTH, Z-WAVE, near field communication ("NFC"), etc., may be used to communicate between the device 1002 and one or more sensors and/or appliances. For example, the device 1002 may be configured to transmit user data and/or environmental data that is collected during a sleep session and/or collected between sleep sessions. For example, via the antenna(s), the input/output device interfaces 1032 may connect to one or more networks 1099/1105 via a wireless local area network (WLAN) (such as Wi-Fi) radio, Bluetooth, and/or wireless network radio, such as a radio capable of communication with a wireless communication network such as a Long-Term Evolution (LTE) network, WiMAX network, 3G network, etc. A wired connection such as Ethernet may also be supported.

The device 1002 and/or server 1120 may also include a command processor (1090/1190) that is configured to execute commands / functions such as measuring user data during a sleep session, determining sleep scores, generating sleep recommendations, etc.

The server may also include a deep neural network 1170, such as a CNN. As discussed above, the deep neural network 1170 may receive unlabeled hypnograms, generate embedding representative of the visual appearance of the hypnogram and determine, based on the embedding, stored and labeled/scored embeddings representative of other hypnograms to determine a sleep score for the received hypnogram. Likewise, the disclosed implementations may also determine one or more recommendations to improve a user sleep score.

In some implementations, multiple devices may be employed in a single system to measure one or more of the user data and/or environment data that is provided to the server 1120 and used to generate a sleep score for a sleep session of a user, and/or generates recommendations for improving a sleep score and corresponding quality of sleep, in accordance with the described implementations. The components of the devices 1002 and server 1120, as illustrated in FIGS. 10 and 11, are exemplary, and may be located as a stand-alone device or may be included, in whole or in part, as a component of a larger device or system.

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the field of computers, communications, energy management, and speech processing should recognize that components and process steps described herein may be interchangeable with other components or steps, or combinations of components or steps, and still achieve the benefits and advantages of the present disclosure. Moreover, it should be apparent to one skilled in the art that the disclosure may be practiced without some or all of the specific details and steps disclosed herein.

Aspects of the disclosed system may be implemented as a computer method or as an article of manufacture such as a memory device or non-transitory computer readable storage medium. The computer readable storage medium may be readable by a computer and may comprise instructions for causing a computer or other device to perform processes described in the present disclosure. The computer readable storage media may be implemented by a volatile computer memory, non-volatile computer memory, hard drive, solid-state memory, flash drive, removable disk and/or other media. In addition, components of one or more of the modules and engines may be implemented in firmware or hardware.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially" as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount. Likewise, the terms "good," "moderate," and "poor" are used to relate to ranges of sleep scores and/or the corresponding quality of sleep. Likewise, the terms "good," and "poor" are used to refer to user behavior and/or environmental conditions that are conducive to improving a sleep score and the corresponding quality of sleep, referred to herein as "good sleep factors," and used to refer to user behavior and/or environmental conditions that may negatively impact a sleep score and the corresponding quality of sleep, referred to herein as "poor sleep factors."

Although the invention has been described and illustrated with respect to illustrative implementations thereof, the foregoing and various other additions and omissions may be made therein and thereto without departing from the spirit and scope of the present disclosure.

What is claimed is:

1. A computer-implemented method, comprising:
   receiving user data collected during a sleep session of a user, wherein the user data indicates one or more of a heartrate of the user, a body temperature of the user, a movement of the user, a perspiration rate of the user, a respiration rate of the user, an activity of the user, a body weight of the user, an age of the user, a gender of the user, a body mass of the user, an SpO2 of the user, or a heart rate variability of the user;
   processing the user data to generate a current visual representation of a current hypnogram that indicates a sleep stage for each of a plurality of epochs of the sleep session;
   subsequent to training a deep neural network, processing, with the deep neural network, the current hypnogram to generate a current embedding vector representative of the current visual representation of the current hypnogram, wherein the current embedding vector represents the current hypnogram in a lower dimensional space such that the current visual representation of the current hypnogram can be reconstructed from the current embedding vector, subject to a loss of accuracy, wherein:
      the deep neural network is trained with data that includes a plurality of labeled hypnograms, each of the plurality of labeled hypnograms labeled with a sleep score indicative of a quality of sleep; and
      the deep neural network is trained to at least:
         receive as an input, a hypnogram;
         generate an embedding vector based at least in part on a visual representation of the hypnogram;
         determine, based at least in part on the embedding vector, at least one stored embedding vector that is within a defined distance of the embedding vector; and
         generate, based at least in part on a stored sleep score corresponding to the at least one stored embedding vector, a sleep score;
   comparing, with the deep neural network, the current embedding vector, using at least one of a k-nearest neighbors approach or a Euclidian distance, to determine a first stored embedding vector that is within the defined distance of the current embedding vector;
   generating, with the deep neural network and based at least in part on a first stored sleep score associated with the first stored embedding vector, a current sleep score, the current sleep score indicating a quality of sleep experienced by the user during the sleep session; and
   sending, for presentation to the user, the current sleep score.

2. The computer-implemented method of claim 1, wherein the deep neural network is a convolutional neural network.

3. The computer-implemented method of claim 1, wherein:
   determining the first stored embedding vector includes determining a plurality of stored embedding vectors that are within the defined distance of the current embedding vector; and
   generating the current sleep score further incudes:
      generating, based on stored sleep scores associated with each of the plurality of stored embedding vectors, the current sleep score.

4. The computer-implemented method of claim 1, wherein determining the first stored embedding vector further includes:
   determining the first stored embedding vector based at least in part on the k-nearest neighbor approach that determines a distance between the current embedding vector and the first stored embedding vector.

5. The computer-implemented method of claim 1, wherein sending the current sleep score includes, sending the current sleep score as a qualitative representation.

6. A method, comprising:

receiving, as input to a network and after the network is trained, a current hypnogram corresponding to a sleep session of a user, wherein:
  the current hypnogram is generated based at least in part on one or more of a heartrate of the user during the sleep session, a body temperature of the user during the sleep session, a movement of the user during the sleep session, a perspiration rate of the user during the sleep session, a respiration rate of the user during the sleep session, an activity of the user during the sleep session, a body weight of the user, an age of the user, a gender of the user, a body mass of the user, an SpO2 of the user during the sleep session, or a heart rate variability of the user during the sleep session;
  the network is trained with data that includes a plurality of hypnograms, at least some of the plurality of hypnograms labeled with a sleep score indicative of a quality of sleep; and
  the network is trained to at least:
    receive as an input, a hypnogram;
    generate an embedding vector based at least in part on a visual representation of the hypnogram;
    determine, based at least in part on the embedding vector, at least one stored embedding vector that is within a defined distance of the embedding vector; and
    generate, based at least in part on a stored sleep score corresponding to the at least one stored embedding vector, a sleep score;
processing, with the network, the current hypnogram to generate a current embedding vector representative of the current hypnogram, wherein the current embedding vector represents the current hypnogram in a lower dimensional space such that the current hypnogram can be reconstructed from the current embedding vector, subject to a loss of accuracy;
comparing, with the network, the current embedding vector, using at least one of a k-nearest neighbor approach or a Euclidian distance, to determine a first stored embedding vector that is similar to the current embedding vector;
generating, with the network and based at least in part on a first stored sleep score associated with the first stored embedding vector, a current sleep score for the current embedding vector;
associating the current sleep score with at least one of the current embedding vector, the current hypnogram, or the user; and
sending, for presentation to the user, an indication of the current sleep score.

7. The method of claim 6, wherein:
determining a stored embedding vector further includes:
  determining a plurality of stored embedding vectors that are within the defined distance of the current embedding vector; and
wherein generating the current sleep score further includes:
  generating, based on stored sleep scores associated with each of the plurality of stored embedding vectors, the current sleep score.

8. The method of claim 6, further comprising:
adjusting the current sleep score based at least in part on one or more results from one or more rule-based algorithms.

9. The method of claim 8, wherein the one or more rule-based algorithms correspond to one or more of a total sleep time, a sleep efficiency, a sleep onset latency, a percentage of deep sleep time, a percentage of REM sleep time, a wakefulness after falling asleep duration, or a number of awakenings during the sleep session.

10. The method of claim 6, further comprising:
  determining that the current sleep score is below a threshold;
  determining an environmental condition that corresponds to a good sleep factor;
  determining that the environmental condition is not associated with the current embedding vector; and
  generating a recommendation for inclusion of the environmental condition by the user.

11. The method of claim 6, further comprising:
  determining that the current sleep score is below a threshold;
  determining a user behavior that corresponds to a good sleep factor;
  determining that the user behavior is not associated with the current embedding vector; and
  generating a recommendation for inclusion of the user behavior by the user.

12. The method of claim 11, wherein the user behavior is determined to correspond to the good sleep factor based at least in part on sleep scores of a plurality of embedding vectors.

13. The method of claim 6, further comprising:
  determining that the current sleep score is below a threshold;
  determining an environmental condition that corresponds to a poor sleep factor;
  determining that the environmental condition is associated with the current embedding vector; and
  generating a recommendation for exclusion of the environmental condition by the user.

14. The method of claim 6, further comprising:
  determining that the current sleep score is below a threshold;
  determining a user behavior that corresponds to a poor sleep factor;
  determining that the user behavior is associated with the current embedding vector; and
  generating a recommendation for exclusion of the user behavior by the user.

15. A computing system, comprising:
one or more processors; and
a memory storing program instructions that, when executed by the one or more processors, cause the one or more processors to at least:
  receive a current hypnogram corresponding to a sleep session of a user, wherein the current hypnogram is generated based at least in part on one or more of a heartrate of the user during the sleep session, a body temperature of the user during the sleep session, a movement of the user during the sleep session, a perspiration rate of the user during the sleep session, a respiration rate of the user during the sleep session, an activity of the user during the sleep session, a body weight of the user, an age of the user, a gender of the user, a body mass of the user, an SpO2 of the user during the sleep session, or a heart rate variability of the user during the sleep session;
  process, with a network and after the network is trained, the current hypnogram to generate a current embedding vector representative of the current hypnogram, wherein the current embedding vector represents the current hypnogram in a lower dimensional space such that the current hypnogram can be reconstructed from the current embedding vector, subject to a loss of accuracy, wherein:

the network is trained with data that includes a plurality of hypnograms, at least some of the plurality of hypnograms labeled with a sleep score indicative of a quality of sleep; and the network is trained to at least:

generate an embedding vector based at least in part on a visual appearance of a hypnogram;

determine, based at least in part on the embedding vector, at least one stored embedding vector that is within a defined distance of the embedding vector; and generate, based at least in part on a stored sleep score corresponding to the at least one stored embedding vector, a sleep score;

compare, with the network, the current embedding vector, using at least one of a k-nearest neighbor approach or a Euclidian distance, to determine a first stored embedding vector that is within the defined distance of the current embedding vector;

generate, with the network, a current sleep score for the current hypnogram based at least in part on a first stored sleep score associated with the first stored embedding vector; and send, for presentation to the user, an indication of the sleep score.

16. The computing system of claim 15, wherein the program instructions that, when executed by the one or more processors, further cause the one or more processors to at least:

determine a recommendation for inclusions of at least one of a user behavior or an environmental condition to improve the current sleep score.

17. The computing system of claim 15, wherein the program instructions that, when executed by the one or more processors, further cause the one or more processors to at least:

determine a plurality of users that are similar to the user;

determine a user behavior that is common to a majority of the plurality of users that is not currently present with the user; and provide a recommendation to the user to include the user behavior.

18. The computing system of claim 15, wherein the program instructions that, when executed by the one or more processors to determine the first stored embedding vector, further include instructions that, when executed by the one or more processors, further cause the one or more processors to at least:

determine the first stored embedding vector based at least in part on the k-nearest neighbor approach that determines a distance between the current embedding vector and the at first stored embedding vector.

19. The computing system of claim 15, wherein the current embedding vector is based at least in part on a visual representation of the current hypnogram.

* * * * *